United States Patent [19]
Hider et al.

[11] Patent Number: 5,968,499
[45] Date of Patent: Oct. 19, 1999

[54] POLYMERIC COMPOUNDS

[75] Inventors: Robert Charles Hider, St. Osyth; Brian Leonard Goodwin, Hampton, both of United Kingdom

[73] Assignee: BTG International Limited, London, United Kingdom

[21] Appl. No.: 08/895,087

[22] Filed: Jul. 15, 1997

Related U.S. Application Data

[63] Continuation of application No. PCT/GB96/00356, Feb. 16, 1996.

[30] Foreign Application Priority Data

Feb. 16, 1995 [GB] United Kingdom ................... 9503061

[51] Int. Cl.$^6$ .................................................. A61K 31/785
[52] U.S. Cl. ..................................... 424/78.08; 424/78.11; 424/78.12; 424/78.16; 424/78.35
[58] Field of Search ............................. 424/78.08, 78.11, 424/78.12, 78.16, 78.35

[56] References Cited

U.S. PATENT DOCUMENTS

| | | | |
|---|---|---|---|
| 2,945,006 | 7/1960 | Minsk et al. . | |
| 3,734,939 | 5/1973 | Schaefer | 260/404.5 |
| 4,071,459 | 1/1978 | Cohen et al. | 252/50 |
| 4,159,898 | 7/1979 | Cohen et al. . | |
| 4,478,984 | 10/1984 | Bryan | 525/333.6 |
| 5,496,545 | 3/1996 | Holmes-Farley et al. | 424/78.11 |
| 5,698,190 | 12/1997 | Hider et al. | 424/78.8 |

FOREIGN PATENT DOCUMENTS

| | | |
|---|---|---|
| 1268210 | 12/1958 | France . |
| 2200457 | 7/1973 | Germany . |
| 62-230806 | 10/1987 | Japan . |
| 867 449 | 12/1958 | United Kingdom . |
| 850281 | 10/1960 | United Kingdom . |
| 857193 | 12/1960 | United Kingdom . |
| 1068543 | 5/1967 | United Kingdom . |
| 1374381 | 11/1974 | United Kingdom . |
| 1486603 | 9/1977 | United Kingdom . |
| WO 92/04385 | 3/1992 | WIPO . |
| WO 94/19379 | 2/1994 | WIPO . |
| WO 95/05184 | 8/1994 | WIPO . |

OTHER PUBLICATIONS

Patent Abstracts of Japan, vol. 12 No. 103 (C–485)(2950) Apr. 5, 1988, abstracting JP–A 62230806.
Patent Abstracts of Japan, vol. 6 No. 4598 (C–77)(4598) 1977, abstracting JP–A 52139050.
Patent Abstracts of Japan, vol. 9 No. 125 (C–283(1848) May 30, 1985, abstracting JP–A 60011509.
Patent Abstracts of Japan, vol. 4 No. 119 (C–22)(601), Aug. 23, 1980, abstracting JP–A 55073706.
Derwent Japan Patent Abstract WPI Accession No. 85–053864/09 abstracting JP–A 60011509.
Derwent Japan Patent Abstract WPI Accession No. 80–684066/39, abstracting JP–A 55104357.
Derwent Japan Patent Abstract WPI Accession No. 80–33546C/19, abstracting JP–A 55042506.
Derwent Japan Patent Abstract WPI Accession No. 80–26758C/15, abstracting SU–A 615087.
A. Akelah and D.C. Sherrington, "Application of Functionalized Polymers in Organic Synthesis" Chem. Rev. 81, 557–587 (1981).
E. Batres and M.L. Hallensleben, "Poly(amidine)s and Poly(guanidine)s—Synthesis and Some Properties", Polymer Bulletin 1, 715–722 (1979).
Chemical Abstracts 85, No. 144224d (1976) abstracting SU–A 523, 112.
Y. Yamamoto and S. Kojima, Chapter 10 "Synthesis and Chemistry of Guanidine Derivatives" in S. Patai and Z. Rappoport (eds.), "The Chemistry of Amidines and Imidates", John Wiley & Sons Ltd., pp. 485–526 (1991).
P.Haddad and P.E. Jackson, "Ion Chromatography: principles and applications", Journal of Chromatography Library 46, 48–52 (1990).
Burt et al., "Ion–Exchange Resins as Potential Phosphate–Binding Agents for Renal Failure Patients: Effect of the Physicochemical Properties of Resins on Phosphate and Bile Salt Binding", Journal of Pharmaceutical Sciences 76, No. 5, 379–383 (1987).
McGary et al., "Polycation as an Alternative Osmotic Agent and Phosphate Binder in Peritoneal Dialysis", Uremia Investigation 8(2), 79–84 (1984–85).
J.A Delmez and E. Slatopolsky, "Hyperphosphatemia: Its Consequences and Treatment in Patients with Chronic Renal Disease", American Journal of Kidney Diseases XIX, No. 4, 303–317 (1992).
G. Semenza, "Chromatographie von Polyelektrolyten V. Aminoäthyl–Cellulose und Guanidinoäthyl–Cellulose", Helv. Chim. Acta 43, 1057–1068 (1960), with partial translation.

*Primary Examiner*—Bernard Lipman
*Attorney, Agent, or Firm*—Nixon & Vanderhye

[57] ABSTRACT

A polystyrene polymer crosslinked by 1.5% to 8% with divinylbenzene based on the total weight of the polymer and having a minimum weight average molecular weight of 10000 wherein 50 to 100% of the aromatic groups of the polystyrene are substituted by at least one —$(R^1)_n$—$NHR^2$ group wherein $R^1$ represents a straight or branched chain alkylene or cycloalkylene group of 1 to 6 carbon atoms and n is 0 or 1 and $NHR^2$ represents a guanidino group of formula —NH—C(=NH)$NH_2$ or a biguanidino group of formula —NH—C(=NH)—NH—C(=NH)—$NH_2$ for use in therapy.

1 Claim, No Drawings

POLYMERIC COMPOUNDS

This is a Continuation of PCT application PCT/GB96/00356, filed Feb. 16, 1996.

FIELD OF THE INVENTION

This invention relates to polymers comprising any one of, or a mixture of, guanidino or biguanidino groups which are capable of binding to phosphate and may be used in the treatment of hyperphosphataemia which may occur for example in patients with kidney disease.

DESCRIPTION OF THE PRIOR ART

Kidney disorders are extremely common and may, if treatment is inadequate, inappropriate or delayed, progress through to end stage renal conditions, the patient subsequently requiring dialysis treatment. Kidney dialysis patients suffer from elevated serum levels of phosphate. In addition, patients who have renal insufficiency frequently develop "kidney stones" which may consist of the two extremely insoluble salts, calcium phosphate and calcium oxalate. High concentrations of both of these anions induce severe toxic effects in such patients. The development of elevated phosphate levels may be minimised in these patients by the addition of aluminium hydroxide, magnesium hydroxide or calcium hydroxide or mixtures of any of these compounds in the diet. However the use of magnesium or calcium hydroxide can lead to acute side effects, hence aluminium hydroxide is the compound which is more commonly used. The presence of aluminium ions in the patient's intestine reduces the uptake of phosphate from the diet through the formation of an insoluble phosphate salt, thus decreasing the availability of the phosphate ion for absorption into the body. The result is a concentration gradient of phosphate from a high level in the blood to a low level in the lumen. Phosphate thus moves out of the blood down this concentration gradient and into the lumen. The continued treatment with aluminium ions hydroxide or related preparations leads to the gradual accumulation of aluminium compounds in body tissues. This is potentially a problem. It is widely thought that the accumulation of aluminium in body tissues may have irreversible effects. The aluminium ions have to be removed by the administration of the compound desferrioxamine, an iron-chelator. This is also known to have side effects, especially in people who are not "iron-overloaded" (for example as a result of blood transfusions). Kidney patients are not iron-over loaded, hence constant use of the compound desferrioxamine to reduce aluminium levels may lead to undesirable side effects in these patients.

It is therefore an object of the present invention to provide a more convenient way of reducing the uptake of phosphate from the diet in kidney patients and reducing phosphate levels in the blood of kidney patients.

It has been found that this may be achieved through the incorporation into a pharmaceutical composition or a foodstuff or an admixture with a foodstuff of a polymer comprising a backbone and guanidino groups attached to the said backbone. Phosphate ions are known to bind to guanidino groups. This attraction is very strong, involving two electrostatic bonds and two stereochemically favourable hydrogen bonds.

The incorporation of guanidino groups into a polymeric structure has been described in GB-A-2276170 which describes a physiologically acceptable polymer comprising a backbone to which are directly or indirectly attached guanidino groups, the polymer having a minimum molecular weight of 10,000. Further description of the prior art will be discussed after the summary of the invention, without which its context would not be clear.

SUMMARY OF THE INVENTION

It has now been found that polystyrene polymers crosslinked by divinylbenzene by 2–8% comprising guanidino and/or biguanidino substituent groups are particularly suitable for the purpose of the present invention without having the side effects associated with aluminium hydroxide treatment.

Accordingly the invention provides a polystyrene polymer crosslinked by 1.5% to 8% with divinylbenzene based on the ratio of the weight of divinylbenzene and styrene used in preparing the polystyrene polymer, the 3-dimensional matrix of the polymer having a minimum weight-average molecular weight of 10000 wherein 50% to 100% of the aromatic groups of the polystyrene are substituted by at least one $-(R^1)_n-NHR^2$ group wherein $R^1$ represents a straight or branched chain alkylene or cycloalkylene group of 1 to 6 carbon atoms and n is 0 or 1 and $-NHR^2$ represents a guanidino group of formula $-NH-C(=NH)NH_2$ or a biguanidino group of formula $-NH-C(=NH)-NH-C(=NH)-NH_2$ for use in therapy.

FURTHER DESCRIPTION OF THE PRIOR ART

Anion exchangers based on guanidine are well known, as the various methods for their preparation. Anion exchangers based on cross-linked polystyrene resins and containing guanidino groups or alkyl guanidino groups are also known. For example, UK Patent 1 374 381 describes a new process for the manufacture of such anion exchange resins. Specific examples include the preparation of guand—the containing resins from polystyrene crosslinked with 8%, 2% and 4% by weight of divinylbenzene. The purpose of making the polymers in UK 1 374 381 is for use as fertiliser.

UK Patent 1 068 543 also describes anion exchange resins comprising guanidino groups and includes examples to polystyrene-divinylbenzene co-polymers. The suggested use of these polymers is in water-conditioning.

Accordingly, although the guanidino-containing polystyrene polymers are relatively well known, their use in therapy has not been previously specified and no preferable degree of crosslinking for therapeutic purposes has been identified.

DESCRIPTION OF THE PREFERRED EMBODIMENTS

The present invention relates to the use of the polymeric compounds of the invention in therapy, for example in pharmaceutical compositions and foodstuffs or as additions to foodstuffs described hereinafter. The invention is of particular interest for the treatment of kidney patients through provision of control of phosphate uptake from the diet and in the promotion of removal of excess phosphate from the blood of such individuals.

As a practical matter, the maximum possible molecular weight of the polymer is defined only as one which cannot be orally administered or which is impractical by, for example, being too large and thus reducing the availability of the guanidino or bignanidino groups for phosphate binding. A molecular weight of $10^{20}$ is envisaged as being about the maximum practical molecular weight. The polymers of the invention, as stated above may incorporate guanidino or biguanidino groups which may be directly substituted into the aromatic rings of the polymer or held on an alkylene "spacer arms" attached to these rings.

By way of clarification, the group $(R^1)_n$—$NHR^2$ will be referred to as guarlidinoalkyl or biguariidinoalkyl where n is 1, depending on the group $R^2$ and guanidino or biguanidino where n is zero. Thus, the $(R^1)_n$ group acts as a "spacer" between the guanidino or biguanidino groups and the polystyrene polymer.

The amount of crosslinking of the polystyrene polymer chains by divinylbenzene is 1.5–8%, preferably 2–6% and more preferably 2–5.5%. In this specification, all references to % crosslinking are related to weight of the styrene and divinylbenzene. The crosslinking is through the polymer backbone and not through the guanidino, biguanidino, or amino groups. The amount of crosslinking of the styrene in the polymer is determined by the manufacture of the polystyrene. It will be appreciated by a person skilled in the art that when referring to the percentage crosslinking of polystyrene by divinylbenzene, that what is generally meant is the percentage of divinylbenzene to styrene in the reaction mixture, and not necessarily the actual percentage crosslinking of the polymer. For example, 2% crosslinked refers to a reaction mix containing 2% divinylbenzene and 98% styrene by weight. Preferably, the crosslinking of the polystyrene polymer is by divinylbenzene but the invention extends to crosslinked polystyrene polymers of any percentage which have the same porosity as that which would be produced by polystyrene crosslinked by up to 8% with divinylbenzene.

Substitution into the aromatic groups of the polystyrene by the —$(R^1)_n$—$NHR^2$ groups of the invention occurs on the aromatic nucleus of the styrene monomers making up the polystyrene polymer. A minimum level is where only 50% of available aromatic nuclei are substituted by only one substituent. The actual substitution positions into the ring and the number of substituents in the ring will depend upon various parameters, for example, the concentrations of the reagents and the reaction conditions. For example, some reaction conditions favour ortho/para substitution and some meta substitution. A skilled person would choose appropriate reaction conditions depending on the type of substitution required.

Preferably, 70–100% of the aromatic nuclei of the polystyrene polymer are substituted with at least one —$(R^1)_n$—$NHR^2$ group of the invention, more preferably 80–100% and even more preferably 90–100%.

The average number of guanidino or biguanidino groups per aromatic rin, of the crosslinked polystyrene polymer may vary from example to example, but will in general lie in the range of just under 1 to just over 2 that is in terms of the average number of substituents per styrene monomer unit. As will be appreciated by a person skilled in the art, the exact value will be dependent upon factors such as the degree of crosslinking of the polymer, the degree of macroporosity and the particular route of synthesis and reaction conditions employed in the preparation of the material. The number of substituents on each aromatic nucleus will be between one and three substituents on average per styrene monomer unit, preferably one or two substituent groups on average and more preferably, only one substituent group on average. Preferably 80–100% and more preferably 90–100% of the substituents are in the para position.

Regarding the group $(R^1)_n$ in the substituent group, n is preferably 1 and is an alkylene chain, straight, branched or cyclic of 1 to 6 carbon atoms. The finction of $(R^1)_n$ is to act as a "spacer arm" between the guanidino or biguanidino group and the polystyrene polymer backbone. The best results are obtained with short spacer arms. Preferably $(R^1)_n$ represents a methylene or ethylene group and more preferably, methylene.

The preferred substituent of the invention is guanidinoalkyl, preferably guanidino methyl. Preferably over 50% of the substituted aromatic nuclei comprise guanidinoalkyl more preferably over 80% and even more preferably 90–100%.

Any unsubstituted aromatic nuclei may remain unsubstituted or optionally they may be substituted up to 3 times per aromatic nucleus with a physiologically inert substituent or mixture of substituents, or with amino groups or amino alkyl groups.

Additionally, physiologically inert substituents may also be present or aromatic nuclei already substituted by the substituent groups of the invention.

As another alternative to physiologically inert substituents, substituted alkylamino groups may be present. Substitution into the amino group may be primary or secondary but not tertiary.

The methods of preparing the polymers useful in the invention are well documented in the art.

Where the guanidino or biguanidino groups are to be directly attached to the aromatic rings of the polymer, that is to say n in the formnula $(R^1)_n$ is zero, synthesis of the polymers may be achieved by following and adapting procedures described in, for example, GB 616 453 or German Patent 1 049 583.

The nitration and subsequent reduction of polystyrene crosslinked with divinylbenzene is discussed in a chapter entitled "The Synthesis of Ion Exchange Resins", Kunin & Myers, John Wiley, 1950, particularly at page 50 wherein reference is made to a process of D'Alelio (U.S. Pat. No. 2,366,007) in which nitration is achieved by nitric acid in the presence of sulphuric acid and reduction by stannous chloride and hydraulic acid.

In what is generally the preferred synthetic route, divinylbenzene-crosslinked polystyrenes ("copolystyrenes") bearing appended aminoalkylene groups are prepared as intermediates. They may be converted from the corresponding chloromethylene co-polymers, for example, via an initial conversion of the chloromethyl compound into the phthlimidomethyl compound by means of a phthalimidation agent such as potassium phthalimide.

Co-polystyrenes bearing chloromethyl substituents can be prepared by appropriate co-polymerisation of vinylbenzyl chloride and divinylbenzene or else by chloromethylation under appropriate conditions of preformed co-polystyrenes, as discussed by Walton (in "Encyclopedia of Analytical Science", Volume 4, Townshend (Ed.), Academic Press 1995; see particularly page 2274). Other halomethyl substituents can be prepared correspondingly.

Haloalkyl-bearing co-polystyrenes can also be prepared by the method of Warth and Fritz (J. Chromatographic Sci. 26, 630–635 (1988)), which is particularly useful in the preparation of polystyrenes where the spacer group has more than one carbon atom. Essentially, the pre-formed colpolymer is reacted with an ω-bromoalk-1-ene (or conceivably another ω-haloalk-1-ene) and trifluoromethylsulphonic acid. The resulting ω-halo-α-methylalkyl substituted polymer can then be phthalimidated as described above.

Alternatively, and preferably, aminoalkylene-bearing co-polymers may be prepared by direct phthalimidoalkylation of a non-functional co-polymer, for example by means of an N-(ω-haloalkyl)-phthalimide such as N-chloromethylphthalimide, as has been described by a number of authors including Zikos and Ferderigos (Tetrahedron Letters 36, 3741–3744 (1995)) and Mitchell etal. (Tetrahedron Letters 42, 3795–3798 (1976)). Higher N-(ω-haloalkyl)-phthalimides, which are available or prepared in the art, can be used to prepare higher N-(ω-haloalkyl)-phthalimido groups. Hydrolysis and/or hydrazinolysis of the phthalimidoalkyl groups yields the corresponding aminoalkyl substituents.

The route of preparation may determine the positioning of the alkylamino groups on the aromatic ring on each monomeric unit.

However the amino substituted polymer is prepared, it may readily be transformed into the corresponding guanidino or biguanidino polymer. Guanidino polymers may be prepared by methods such as those described in GB 1 068 543 and GB 1 374 381 or (with appropriate adaptions) by methods chosen from those summarised by Yamamoto and Kojima in "The Chemistry of the Amidines and Imidates", Patai and Rappoport, Eds., John Wiley, 1991, Chapter (10). Biguanidino-bearing polymers can be prepared either from the corresponding monoguanidino polymers, by reacting them with cyanamide, or from the amino-bearing polymers by reaction with dicyandiamide.

An example of a preferred route of preparation is now described.

In order to prepare the polymer from polystyrene via an aminoalkyl aminomethyl for example, intermediate, the first step is a phthalimidomethylation step. This can be achieved in, for example, the following way. Firstly, (the aromatic ring of the styrene unit in the polymer is phthalimidomethylated by N-chloromethylphthalimide) using trifluoroacetic acid and dichloroethane with a suitable catalyst, for example a trifluoromethanesulphonic acid catalyst, starlnic chloride or ferric chloride. This step produces a phthalidomethylpolystyrene as shown below.

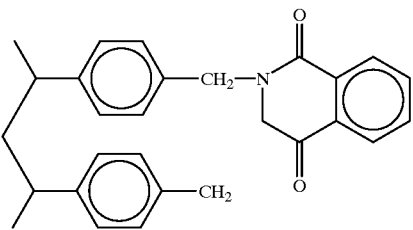

As discussed above the aromatic nucleus may be solely substituted at the para position as shown, but depending on the reaction conditions, may also be substituted in the ortho and meta positions on the benzene ring.

Where possible, para substitution is preferred, or a mixture of ortho and para. If there is only an average of one substituent in the aromatic ring then this is preferably substantially all in the para position, preferably at least 70% and more preferably 90%.

In order to produce aminomethylpolystyrene, it has surprisingly been found that the usual next stage of hydrazinolysis is generally not sufficient. Thus, in addition to the hydrazinolysis reaction it is generally necessary to perform a hydrolysis step preferably with HCl as well.

The aminomethylpolystyrene thus produced can be converted to guanidinomethylpolystyrene by reaction with for example cyanamide or via a pyrazole intermediate or biguanidinomethylpolystyrene by reaction with dicyandiamide. Substitution into the aminomethyl group prior to conversion into the guanidino or biguanidino polymer of the invention may be carried out. In this case, substitution may be either primary or secondary, but not tertiary. If the amino methyl group is substituted, preferably the substituent is a simple group such as alkyl ($C_1$–$C_4$). However a skilled person would realise that, as long as the final conversion to the guanidino or biguanidino resin was sterically not hindered, and the phosphate binding properties not interfered with, any suitable substitution could be made.

It will be appreciated that in some circumstances the conversion of the aminomethylpolystyrene intermediate to guanidinomethylpolystyrene or biguanidinomethylpolystyrene may be less than 100%. This is not disadvantageous since aminomethylpolystyrene is also capable of binding phosphate. Preferably however, the conversion rate is 50–100% and more preferably between 80 and 100% and even more preferably between 90 and 100%.

The guanidino or biguanidino groups are attached to the polymer backbone (this backbone includes the alkylene group) by means of chemical bonding through the terminal NH group of the guanidino group ($NH_2$—C(=NH)—NH—) or biguanidino group ($NH_2$—C(=NH)—NH—C(=NH)—NH—). The guanidino, or biguanidino, is attached to the alkylene spacer group of the polymer backbone.

It has been found that the polymers of the invention are able preferably to bind phosphate anions in vitro than other physiologically important anions. The polymers of the invention thus have a particular use for the prevention of phosphate uptake from the diet and/or also the removal of excess phosphate from the blood of those patients with deficient kidneys since the binding of phosphate in the intestine from the diet disturbs the body equilibrium and effects movement of phosphate from the bloodstream into the intestine. The polymers of the invention may be administered to the patients orally either as foodstuff or as an addition to a foodstuff, or as pharmaceutical composition.

According to a further aspect of the invention there is provided a foodstuff or an addition to a foodstuff comprising a polymer of the invention. Such foodstuffs may take a variety of forms, for example taking the form of conventional human food.

According to a further aspect of the invention there is provided a pharmaceutical composition adapted for oral administration comprising a polymer of the invention in association with a pharmaceutically acceptable diluent or carrier.

The guanidino amino or biguanidino group-containing polymer of the invention may be formulated in a pharmaceutical composition by a variety of methods. The pharmaceutical composition will normally be orally administered since it should be present in the intestine of the patient. Although compositions incorporating a liquid diluent may be used for oral administration, it is also possible to use compositions incorporating a solid carrier material such as starch, lactose, or dextrin. Such solid compositions may conveniently be of a formed type, for example as tablets, capsules, etc.

The pharmaceutical compositions, foodstuffs or addition for foodstuffs may be formulated in unit dosage form, i.e. in the form of discrete portions containing a unit dose, or a multiple or sub-unit of a unit dose. The daily dosage of the polymer will of course depend upon individual circumstances, and the severity of kidney disease in the patient, as well as the chemical structure of the alkylguanidino, alkylamino or alkylbiguanidino group-containing polymer. By way of guidance a daily dosage in terms of guanidine would be in the range 5 g to 50 g, preferably 5 g–25 g and more preferably 10–20 g, and thus the amount of polymer can be calculated accordingly.

According to a further aspect of the invention there is provided a method of treatment of a patient which comprises administering to said patient a polymer described hereinbefore in order to control phosphate uptake from the diet and/or to remove excess phosphate from the bloodstream.

According to a further aspect of the invention there is provided the use of a polymer described hereinbefore for the manufacture of a medicament for the treatment of a patient in order to control phosphate uptake from the diet and/or to remove excess phosphate from the bloodstream.

An alternative method of utilisation of the polymers of the invention is to include them in part of the dialysis routine of patients with renal insufficiency. In dialysis, the blood is essentially filtered of impurities before being returned to the patient. As part of this routine, the blood may be passed through, for example, a cartridge pre-loaded with polymers of the invention so that excess phosphate may be removed from the blood.

According to a further aspect of the invention there is provided a method of removing excess phosphate from the blood comprising the steps of removing the blood from the patient and exposing the blood to a polymer described hereinbefore. There is also provided for use in blood treatment, an appropriately dimensioned container including a polymer of the invention, in which blood can be treated to remove excess phosphate. The container includes means to connect to the patient either directly or indirectly, preferably blood entrance and exit means which may be for example flexible tubing.

The invention will now be illustrated by way of Example.

EXAMPLE 1

Swelling of Polystyrene in Dichloromethane

The concept of working with crosslinked resins is to enable the resin to remain as an insoluble material in the gut when functioning as a scavenger for phosphate. The degree of crosslinking places constraints on the suitability of the resin, both in the process of scavenging for phosphate and in the manufacturing process.

If the degree of crosslinking is too small then the resin will swell to an unacceptable extent and a small proportion will not even be crosslinked, thus the guanidino resin prepared from the non-crosslinked portion will be partially soluble in water.

If the degree of crosslinking is too great, the resin will not swell sufficiently during the manufacturing process to permit the adequate access of reagents, nor will the guanidino resin prepared from it swell sufficiently in water to permit adequate access of phosphate ions.

To access the range of acceptable degrees of crosslinking, the amount of swelling of a variety of polystyrene resins was measured. The resins were placed in flat bottomed tubes and the depth was measured. An excess of dichloromethane was added and the resins were left to swell for one hour, with agitation to release trapped bubbles and enable the floating resin beds to settle. The depth of resin prior to and after addition of the solvent was measured. It was found that the degree to which the resin expanded was inversely proportional to the degree of crosslinking.

The results are shown in Table 1 below:

TABLE 1

Swelling of polystyrene in dichloromethane

| Crosslinking (%) | Source | % Increase | % Increase multiplied by % Crosslinking |
|---|---|---|---|
| 1 | Fluka | 460 | 460 |
| 2 | Purolite | 225 | 450 |
| 4 | Fluka | 115 | 460 |
| 5.3 | Purolite | 88 | 465 |
| 20 | Fluka | 26 | 520 |

The purpose of this experiment was to indicate the problems when handling low crosslinking and the difficulties of carrying out synthetic reactions due to lack of swelling at high % crosslinking.

EXAMPLE 2

General Preparation of Guanidinomethylpolystyrene

1. Phthalimidation

Using the following starting materials guanidino containing resins were prepared:

1. Polystyrene (1%, 2%, 4% and 20% crosslinked) was obtained from Fluka Chemicals Ltd. The bead size was 200–400 mesh.
2. Polystyrene (2% crosslinked) was obtained from Purolite International Ltd. The median diameter was approximately 0.5 mm.
3. Polystyrene (5.3% crosslinked) was obtained from Purolite. The particle size was in the range 0.2–0.425 mm with a mean diameter of 0.28–0.35 mm. It was screen size BSS Standard Mesh 44–150.

The conversion into phthalimidomethylpolystyrene was done in one of three ways.

Route A

One of the procedure described in Mitchell et al., Tetrahedron Letters, 1976, 3795–3798.

Polystyrene beads, 5.3% crosslinked, were stirred with N-chloromethylphthalimide in a 1:1 v/v mixture of dichloromethane and trifluoroacetic acid (typically 10 g of resin and 50 ml of solvent) with 1.2 ml of trifluoromethanesulphonic acid as catalyst. Excess reagent etc. were washed out with dichloromethane-trifluoroacetic acid mixture, dichloromethane, ethanol, then methanol. Uptake of the phthalimide moiety was extensive, based on weight change. Results for different incubation times, temperatures and quantities of reagent are shown in Table 2. This procedure clearly gives a good uptake of phthalimido moiety, except for the highly crosslinked resin where the uptake was very low.

TABLE 2

Uptake of phthalimidomethyl (PM) groups by crosslinked polystyrene

| Expt. | Crosslink % | Temp | Time | PM/g used | PM/g uptake | % uptake |
|---|---|---|---|---|---|---|
| 1 | 1 | RT | 6.5 h | 5 mmol | 1.8 mmol | 36 |
| 2 |   | RT | 22 h | 5 mmol | 4.05 mmol | 81 |
| 3 |   | RT | 65 h | 15 mmol | 11.3 mmol | 75 |
| 4 | 2 | RT | 18 h | 5 mmol | 4.25 mmol | 85 |
| 5 | 4 | RT | 42 h | 5 mmol | 2.55 mmol | 51 |
| 6 | 5.3 | RT | 65 h | 13.8 mmol | 5.4 mmol | 39 |
| 7 |   | RT | 65 h | 10.6 mmol | 5.55 mmol* | 52 |

TABLE 2-continued

Uptake of phthalimidomethyl (PM) groups by crosslinked polystyrene

| Expt. | Crosslink % | Temp | Time | PM/g used | PM/g uptake | % uptake |
|---|---|---|---|---|---|---|
| 8 | | RT Reflux | 65 h+ 24h** | 13.8 mmol | 11.6 mmol | 84 |
| 9 | 20 | RT | 22 h | 5 mmol | 0.05 mmol | 1 |

**Much of the solvent was taken up; the beads became red-black. Values are based on weight change.

Route B

A modification to the procedure described in Mitchell et al., Tetrahedron Letters, 1976, 3795–3798 differs from the standard method (described in A above) in that anhydrous stannic chloride was used as a catalyst. A typical reaction using 10 g of polystyrene was carried out in 40 ml of dichloroethane with 30 g of chloromethylphthalimide, using 1.2 ml of stannic chloride as catalyst and refluxing overnight. The phthalimidation progresses quickly with rapid evolution of HCl, and quantitative and qualitative (IR) results showed that it followed the same path as the standard reaction.

This procedure results in less collateral chemical damage to the resin than does the standard method. After phthalimiomethylation the beads are deep red (reddish black in the standard method), and the amount of solvent taken up by the beads is increased, suggesting that the interstices are more open. If the resin is heated dry at 100° or hotter it darkens considerably. If the reaction mixture is stirred with water, the beads turn an opalescent pink. This procedure has the advantage over route (A) in that it uses cheaper reagents and omits the use of highly toxic reagents.

Route C

A similar procedure to (B) above was carried out except that ferric chloride was used as a catalyst. This is based on one of the procedures described in Zikos and Ferderigos etrahedron Letters, 1995, 36, 3741–3744.

A 10 g portion of 2% crosslinked polystyrene was heated for 26 hours at reflux with 25 g of chloromethylphthalimide, 3.0 g of ferric chloride and 60 ml of dichloromethane. HCl was evolved, but not as rapidly as with starnnic chloride. The beads turned deep red, almost black. The reaction was terminated by stieing with 200 ml of water. The resin was further washed with water and methanol, and then dried. Yield of brown resin 27.1 g. The IR spectrum was almost identical with that for resin prepared by Route B.

This procedure has the advantage over (B) above in that the catalyst is a cheaper alternative to stannic chloride and the ferric chloride catalyst, if retained by the resin is non-toxic.

2. Removal of Phthalimide Moiety—Preparation of Aminomethylated Resin

This method is applicable to resins of all degrees of crosslinking,. This was carried out in 2 stages. Phthalimidomethylpolystyrene was heated with a 20% solution of hydrazine in dimethylformnamide at 110° overnight. This removed about 80% of the protecting phthalic acid. The partly lysed resin was then heated at about 100° overnight with concentrated HCl. An aminomethyl resin was thus produced from which essentially all the phthalimido group was removed.

3. Guanidination Reaction

This procedure basically involves the condensation of the amino groups with cyanamide to form guanidino groups. This method is applicable to resins of all degrees of crosslinking.

Aminomethylpolystyrene (HCl salt) was heated at 100° overnight with 2 parts of 50% cyanamide solution and 3 parts of water. The product has a phosphate uptake of about 2.5 mmol/gy, (by equilibration with phosphoric acid followed by a water wash).

An alternative method of guanidination is to use 1-guanidino-3,5-dimethylpyrazole as a guanidinating reagent.

In order to prepare 1-guanidino-3,5-dimethylpyrazole, a solution of 50 g of 2,4-pentanedione in 140 ml of 50% ethanol was refluxed and 68.0 g of aminoguanidine nitrate was added in portions over 1¾ hours and refluxing was continued for a further 2¼ hours. Upon cooling, much of the product separated as white needles and some more was obtained by evaporating the mother liquors and crystallising the residue from 50% ethanol.

In order to use the 1-guanidino-3,5-dimethylpyrazole in guanidination, the following procedure was carried out.

A portion of 0.94 g of aminomethyl resin HCl salt and 1.96 g 1-guanidino-3,5-dimethylpyrazole (about a 3-fold excess) in 20 ml of water was adjusted to pH 8.75 with NaOH and refluxed overnight. After cleanup (including an alkaline wash) and drying the yield was 0.94 g. The weight sugoests that the reaction may have been incomplete. The infra-red spectrum closely resembled that for guanidinated resin prepared using cyanamide, with some differences that suggest that this procedure may bring about fewer side reactions than cyanamide.

EXAMPLE 3

General Prepparation of Biguanidinomethylpolystyrene

The method of Example 2 was followed up to and including step 2. Then the following biguanylation reaction was performed.

Biguanylation

This reaction was carried out using both the fully saturated acetate salt, and the partial acetate salt prepared by equilibration of resin with acetate at pH 9.3 (the pK of benzylamine), and refluxing ovenight with an aqueous solution of dicyandiamide. The infra-red spectrum of the product from the full acetate salt showed a greater chance from that of the starting material than did the pH 9.3 resin, suggesting that a greater degree of reaction occurred with the full acetate salt of the resin. At the end of the reaction the pH was 7.3. Use of finely powdered resin showed a greater change in IR spectrum than observed with these resins but the phosphate uptake profile suggested that the reaction was still incomplete. In this preparation, 4.99 g of aminomethyl resin HCl and 2.30 g of dicyandiamide were used, to yield 3.51 g of biguanidinomethyl resin, free base.

In a possible new procedure, a portion of aminomethyl resin (1 g) as its acetate salt was refluxed with 1.52 g of dicyandiamide in 10 ml of n-butanol overnight. After cleanup the resin gave an infra-red spectrum that differed significantly from those obtained following the former method, and which suggested that the reaction was approaching completion. The advantage of this procedure is that the use of n-butanol opposed to water enables the reaction temperature to be elevated. This helps to ensure the reaction approaches completion.

EXAMPLE 4

Preparation of a Guanidino-Containing 1% Crosslinked Resin

1% crosslinked polystyrene resin beads (10 g), 200–400 mesh obtained from Fluka were stirred with a solution of 10 g of N-chloromethylphthalimide in 50 ml each of dichloromethane and trifluoroacetic acid and 1.2 ml of trifluoromethanesulphonic acid. Overnight all the solvent was taken up into the resin beads which had become straw coloured. After 22 hours dichloromethane was added, filtered and washed slowly with dichloromethane, ethanol and methanol in succession. Dry weight 16.4 g. This was the phthalimido-containing resin.

5.1 g of this resin was refluxed with 40 ml of 30% aqueous methylamine. After 7 hours the infra-red spectrum demonstrated an extensive disappearance of carbonyl bands. It was filtered, washed with ethanol and dried and yielded 3.3 g. The HCl hydrolysis step appeared to have only a minimal effect on this resin which still contained a small amount of phthalimido groups.

The resin was suspended in diluted HCl for 2 hours, washed thoroughly with water, suspended in 15 ml of 15% cyanamide in water and refluxed overnight, filtered, washed with boiling water and dried. Yield 4.05 g. The product was appreciably hygroscopic and it tended to cake.

This was a moderately good procedure.

EXAMPLE 5

Phosphate Binding Experiments—5.3% Crosslinked Guandino-Containing Resin Prepared via Phthalimidomethyl Intermediate a) Anion Competition Studies The purpose of these experiments was to determine the manner in which anions compete with phosphate at pH 8 for uptake by guanidino-based resin. The resin beads prepared from 5.3% crosslinked polystyrene proved to be too large for ready equilibration with buffers passed through a shallow bed. However, crushed resin (estimated to be 200 mesh and finer) was satisfactory; this was demonstrated by the complete uptake of phosphate at 1 mM concentration passed through a bed about 1 cm deep at a flow rate of about 1 cm/min.

Three experiments were carried out in buffers at pH 8.0 containing 25 mM anions. In the first, solutions of anions were passed through columns of phosphate-loaded crushed guanidinomethyl resin, in the second a similar resin was stirred with solutions of these anions until equilibration had been reached, and in the third and possibly most significant experiment 1 mM phosphate solutions containing the anions were passed through beds of free guanidinomethyl resin base. The same picture was obtained with all three approaches. Acetate interfered least with phosphate uptake, and chloride was also found to be relatively ineffective. Bicarbonate interferes slightly more, but as expected sulphate competes effectively with phosphate uptake.

b) Phosphate Elution Profile

The guanidino-containing resin was prepared by stirring the crushed guanidino resin (free base) in an excess of phosphate buffer, stirred and adjusted to pH 8 until equilibrated, filtered, washed and dried 0.3 g (±c.1%) portions were placed in columns (1 cm bore) and eluted at about 10 µl/second Tris buffer 10 mM, pH 8 containing 6.7 mM chloride was used in all eluting solutions, and except for chloride elution the ion concentration, 25 mM in each case, was additional to the chloride in the Tris; for the chloride experiment the final concentration was 25 mM. 3×80 ml aliquots of these anions were collected and assayed for phosphate. Bicarbonate and acetate buffers were adjusted to pH 8 prior to use (which required a trace of acid only). The resin contained 1.37 mmol/g, of phosphate. Results are expressed as % of the total phosphate present in successive eluates and are shown in Table 3 below:

TABLE 3

Phosphate elution from crushed guanidinomethyl resin

| Eluant | Eluate 1 | Eluate 2 | Eluate 3 | Total Eluted |
| --- | --- | --- | --- | --- |
| Tris only | 28.7 | 8.1 | 4.4 | 41.2 |
| Chloride | 45.2 | 8.3 | 5.6 | 59.1 |
| Sulphate | 86.2 | 10.1 | 3.2 | 99.5 |
| Bicarbonate | 53.3 | 12.4 | 6.8 | 72.5 |
| Acetate | 40.0 | 8.9 | 5.2 | 54.1 |

The results demonstrate that, in decreasing order of efficiency, sulphate, bicarbonate, chloride and acetate displace phosphate.

c) Equilibration Tests with Buffers

Resin was prepared by soaking 5.3% crosslinked guanidinomethyl resin beads (free base) in excess dilute phosphoric acid, decanting off most of the excess acid, adding water and then adjusting the pH to 8 with NaOH and stirring until thoroughly equilibrated. The resin was then filtered, washed and dried. It contained 1820 µmol phosphate/g. Portions of this (1 g/100 ml, i.e. with a phosphate content somewhat less than the molar ionic content of the solution) were stirred overnight with 25 mM anion in 10 mM Tris, pH 8.0, containing 5 mM Cl$^-$. The phosphate concentration in the solution was measured. The results are shown in Table 4 below.

TABLE 4

Equilibration tests with buffers

| Ion | Phosphate concentration | % Phosphate released |
| --- | --- | --- |
| Cl$^-$ | 4.4 mM | 25 |
| SO$_4^{2-}$ | 12.5 mM | 68 |
| OAc$^-$ | 3.45 mM | 19 |
| HCO$_3^-$ | 8.25 mM | 45 | d) Phosphate Uptake by Crushed Guanidinomethyl Resin Beads in the Presence of Inorganic Salts Phosphate buffer, 1.047 mM, containing 25 mM added inorganic salt, pH 8.0 was passed through the resin in a 1 cm bore column (about 10 µl/second ). The depth of resin was about 1 cm. The effluent was collected in six 100 ml fractions. The results are shown in Table 5 below. To determine the uptake for each fraction the phosphate concentration in each fraction was subtracted from the initial concentration and the result was multiplied by the volume of the fraction. In some cases, the concentration of phosphate was greater in the effluent than in the eluting solution towards the end of the experiment; the anion under test was eluting phosphate that had already been taken up by the resin.

TABLE 5

| Fraction No. | Cumulative uptake of phosphate (µmol) | | | | |
| --- | --- | --- | --- | --- | --- |
| | No added salt | Cl$^-$ | SO$_4^{2-}$ | HCO$_3^-$ | OAc$^-$ |
| 1 | 105* | 104* | 26 | 72 | 104* |
| 2 | 209* | 178 | 15 | 129 | 208 |
| 3 | 281 | 206 | 11 | 167 | 273 |
| 4 | 322 | 217 | 10 | 141 | 296 |
| 5 | 353 | 225 | 9 | 120 | 310 |
| 6 | 373 | 232 | 8 | 110 | 326 |

*Phosphate taken up quantitatively.

e) Phosphate Uptake Experiments: 5.3% Crosslinked Guanidinomethyl Polystyrene

A batch of guanidinomethylpolystyrene, 5.3% crosslinked was prepared as described in Example 2, and split into two parts. Each part was equilibrated with excess phosphate at pH 2 and 6. The phosphate content of the pH 2 resin was 2.10 and the pH 6 resin 1.59 mmol.

Phosphate elution from guanidinated resins at pH 2 and 6 respectively

Columns were prepared with 0.5 g (±2 mg) of the above resins. The columns were eluted with 25 mM chloride or sulphate at pH 2 and 6 and fractions of 80 ml were collected. The results are shown in Table 6 below.

TABLE 6

Phosphated elution from 5.3% crosslinked guanidinomethyl polystyrene

| Fraction | pH2 Chloride | Sulphate | pH6 Chloride | Sulphate |
|---|---|---|---|---|
| 1 | 93.4 | 94.7 | 62.4 | 91.6 |
| 2 | 98.8 | 99.0 | 71.6 | 96.6 |
| 3 | 98.9 | 99.1 | 77.2 | 98.1 |

These results which are the cumulative % of phosphate released, demonstrate that phosphate elutes more readily at acidic pH than at pH 6. Even under these conditions there is a small residual amount of phosphate that is difficult to elute.

EXAMPLE 6

Preparation of 2% Crosslinked Guanidine-Containing Resin (i) Phthalimidation

Using 2% crosslinked polystyrene obtained from Fluka, phthalimidation was carried out following Route B described in Example 1 above.

The first experiment tested the extent of reaction between resin and N-chloromethylphthalimide. Five replicates were carried out, each using 2 g of polystyrene, 15 ml dichloroethane, 0.25 ml of stannic chloride, and varying amounts of N-chloromethylphthalimide in the range of 2–6 g. After refluxing overnight each reaction mixture was washed with 25 ml of dichloromethane and stirred for about 3 hours to extract residual reagent from the resin, filtered and washed successively with dichloromethane, acetone, water and acetone, and finally dried at about 80°. Weighed portions were then dried overnight at above 100°; they darkened to nearly black, and from the weight the total dry weight of the purified resin was calculated. Pigment that developed on mild heating over an extended time period can be removed by leaching out with dichloromethane.

This experiment was carried out to enable phosphate uptake to be determined on the derived guanidinomethyl resins. The gravimetric indicators for both these experiments were consistent with a nearly quantitative uptake of N-chloromethylphthalimide up to a substitution ratio of about 1.5/aromatic nucleus (this contrasts with the slightly lower uptake of 85–91% using 5.3% crosslinked polystyrene, and about 70% with the latter resin using Route A, Example 2). There was a small contribution to the weight increase from tin uptake. Solvation was negligible when the resin was finally dried at about 80°. Uptake appears to be appreciably less than quantitative when a small ratio of chloromethylphthalimide to polystyrene was used.

Phthalimidation can be conveniently carried out with 6 volumes of dichloroethane to 1 part (by weight) of polystyrene when an uptake of chloromethylphthalimide of about 1.15 mol/aromatic nucleus is sought. This leaves about 1 volume of solvent that can be decanted at the end of the reaction, and is sufficient to allow the resin to be stirred with ease. The weight gain is consistent with almost quantitative reaction.

(ii) Conversion to Aminomethylpolystyrene

After hydrazinolysis followed by hydrolysis for 48 hours with concentrated HCl the infra-red spectra showed that, with the possible exception of the most lightly loaded resin, an amino absorption at 1600 cm$^{-1}$ appears, and is strongest, relative to other absorptions in the fingerprint region for resins with a loading of 1.0–1.2 mol/nucleus.

(iii) Further Synthetic Steps

Guanidinomethyl derivatives were prepared from the above resins as described in Example 2. Phosphate uptake was measured on these resins. It was noted that the resin swelled appreciably on treatment with phosphoric acid; most of the swelling was reversed when the excess phosphoric acid was washed out, which suggests that at high phosphoric acid concentration a large amount of phosphate is loosely bound to the resin.

The results are showvn in Table 7 below.

The results in Table 7 demonstrate the relationship between the amount of N-chloromethylphthalimide (CMP) taken up by polystyrene in Route B and the phosphate capacity of the final guanidinomethylpolystyrene. The phosphate uptake is proportional to the amount of CMP that reacts with the polystyrene, which is a measure of the aminomethyl groups available for guanidination.

TABLE 7

Phosphate uptake by 2% crosslinked polystyrene resins

| Experiment | A | B | C | D | E | F | G |
|---|---|---|---|---|---|---|---|
| 1 | 5.1 | 4.65 | 0.48 | 1.21 | 1.62 | 0.32 | 0.35 |
| 2 | 7.7 | 7.75 | 0.51 | 1.70 | 2.65 | 0.34 | 0.34 |
| 3 | 10.25 | 10.4 | 1.08 | 1.91 | 3.36 | 0.32 | 0.31 |
| 4 | 12.7 | 12.5 | 1.30 | 2.17 | 4.24 | 0.33 | 0.34 |
| 5 | 15.4 | 15.1 | 1.57 | 2.66 | 4.84 | 0.31 | 0.32 |

A. mmol of CMP used/g of polystyrene in the synthesis.

B. mmol of CMP taken up/g of polystyrene in the synthesis, based on weight gain.

C. number of molecules of CMP taken up per aromatic nucleus.

D. mmol of phosphate taken up/g of guanidinomethylpolystyrene.

E. mmol of phosphate taken up/g of polystyrene used in the synthesis.

F. mmol of phosphate taken up/mmol of CMP used in the synthesis.

G. mmol of phosphate taken up/mmol of CMP taken up in the synthesis.

EXAMPLE 7 pH Phosphate Uptake Profiles 2% Guanidino and Biguanidino Containing Resins Prepared via a Phthalimido Intermediate 1 g of each powdered resin was initially equilibrated with 50 ml of 2% phosphoric acid. The pH was then raised in steps from 4–11 by the addition of NaOH, with stirring at each step for a minimum of 15 minutes to ensure equilibration. An aliquot was withdrawn at each pH, filtered and the resin was washed with water to remove unbound phosphate and then dried. A weighed portion of each batch was suspended in 10 ml of 2 m NaOH to dissolve the phosphate for assay. The results are shown in Tables 8, 9 and 10 below.

The polymers tested were 2% crosslinked, the aminomethylpolystyrene intermediate being prepared via the phthalimidation procedure were 2% crosslinked guanidinomethyl polystyrene and biguanidinomethylpolystyrene prepared as described in Examples 2 and 3 above.

TABLE 8

Guanidinomethyl resin

| pH | Uptake* | Uptake as % of pH4 uptake |
|---|---|---|
| 4.03 | 2.26 | |
| 4.92 | 2.08 | 92 |
| 5.94 | 1.74 | 77 |
| 6.66 | 1.51 | 67 |
| 7.38 | 1.38 | 61 |
| 8.09 | 1.35 | 60 |
| 8.91 | 1.17 | 52 |
| 9.74 | 1.25 | 55 |
| 10.33 | 0.94 | 42 |
| 10.99 | 0.76 | 34 |

*mmol/g of resin base

TABLE 9 pH-phosphate uptake profile for 2% crosslinked Biguanyl resin A

| pH | Uptake* | uptake as % of pH4 uptake |
|---|---|---|
| 4.02 | 3.95 | |
| 4.88 | 3.59 | 91 |
| 5.80 | 3.06 | 77 |
| 6.58 | 2.59 | 66 |
| 7.28 | 2.39 | 61 |
| 8.00 | 2.21 | 56 |
| 8.68 | 1.80 | 46 |
| 9.27 | 1.12 | 28 |
| 9.99 | 0.54 | 14 |
| 10.99 | 0.28 | 7.1 |

*mmol/g of resin base.

TABLE 10 pH-phosphate uptake profile for 2% crosslinked Biguanyl resin B

| pH | Uptake* | uptake as % of pH4 uptake |
|---|---|---|
| 4.00 | 1.65 | |
| 4.89 | 1.57 | 95 |
| 5.90 | 1.31 | 79 |
| 6.00 | 1.10 | 67 |
| 7.35 | 0.89 | 54 |
| 8.04 | 0.76 | 46 |
| 8.79 | 0.69 | 42 |
| 9.54 | 0.645 | 39 |
| 10.29 | 0.49 | 30 |
| 11.94 | 0.565 | 34 |

*mmol/g of resin base

Biguanyl resin A was prepared from aminomethyl resin, acetate salt with dicyandiamide at 100° overnight. The degree of biguanylation was probably low. Resin B was prepared at reflux temperature overnight in n-butanol.

EXAMPLE 8

Competition Between Phosphate and Chloride
Complete Elution by Chloride of Phosphate Bound
on to 2% Crosslinked Polystyrene Containing
Guanidino and Biguanidino Groups Portions of 2% crosslinked guanidinomethyl and biguanidinomethyl containing polystyrene polymers described in Example 2 were saturated with phosphate at pH 8.0. 1 g of the powdered resin was equilibrated in 50 ml of phosphoric acid at pH 8.0. The resin was washed and dried to remove unbound phosphate and portions containing about 0.60–0.65 mmol of phosphate were placed in 1 cm bore columns.

The resin was then eluted with 2×30 ml of 25 mM NaCl (Eluate A-B), 4×50 ml of 100 mM (Eluate C-F) and up to 4×250 mM NaCl (Eluate G-J), the elutions being terminated when the amount of eluted phosphate became too small. The residual phosphate was the eluted with 1 M NaOh (Eluate X). To assess the effect of the chloride, a function Z was calculated.

$$Z = \frac{[Cl^-] \times P.res}{[PL_4{}^{3-}] \times P.tot}$$

where [Cl⁻]=the chloride concentration used to elute the phosphate $[PO_4{}^{3-}]$=the phsophate copncentration in the eluate (both expressed as molar concentration)

p.res=the mean amount of phosphate on the resin p.tot=the total amount of phosphate on the resin prior to elution.

The latter two terms make an approximate compensation for the loss of phosphate during previous elution steps. The larger the Z value, the more firmly phosphate is retained on the resin in the presence of chloride.

The results are shown in Table 11 and 12 below.

TABLE 11

Competition between phosphate and chloride.
Column elution of phosphate loaded guanidinomethyl resin

| | V | X | Y | Z |
|---|---|---|---|---|
| A | 4.55 | 135 | 77.2 | 4.85 |
| B | 1.32 | 40 | 70.4 | 13.9 |
| C | 3.55 | 177 | 39.8 | 15.5 |
| D | 0.92 | 46 | 31.9 | 39 |
| E | 0.55 | 27 | 27.2 | 54 |
| F | 0.45 | 22 | 23.3 | 56 |
| G | 1.36 | 68 | 11.5 | 32 |
| H | 0.40 | 20 | 8.1 | 61 |
| I | 0.193 | 9.7 | 6.4 | 94 |
| J | 0.125 | 6.25 | 5.4 | 118 |
| NaOH wash | — | 31.2 | | |

TABLE 12

Competition between phosphate and chloride.
Column elution of phosphate loaded biguanidinomethyl resin A

| | V | X | Y | Z |
|---|---|---|---|---|
| A | 4.38 | 132 | 78.8 | 5.05 |
| B | 1.70 | 51 | 70.6 | 11.0 |
| C | 4.36 | 218 | 35.7 | 12.2 |
| D | 1.71 | 86 | 22.0 | 16.8 |
| E | 1.05 | 52 | 13.6 | 17.0 |
| F | 0.66 | 33 | 8.3 | 16.8 |
| G | 0.68 | 34 | 2.9 | 24.4 |
| H | 0.048 | 2.4 | 2.5 | — |
| I | 0.016 | 0.78 | 2.4 | — |
| J | — | — | — | — |
| NaOH wash | — | 15.1 | | |

V=concentration of phosphate in the eluate
X=Total phosphate in the eluate $\mu$mol x⁻6
Y=% phosphate remaining on resin at end of elution step

EXAMPLE 9

Phosphate Uptake Experiments Comparison of Cyanamide with 1-guanidino-3 5-dimethylpyrazole as Guanidinating Reagents with Commercially Available Macroporous Aminomethylpolystyrene a) Preparation of Resins 2% crosslinked polystyrene containing guanidino and biguanidino groups were prepared from 2% crosslinked aminomethylpolystyrene purchased from Purolite International Ltd.

The 2% crosslinked aminomethyl polystyrene obtained from Purolite International Ltd was believed to have been prepared via a chloromethyl intermediate. Guanidination was via the cyanamide or pyrazole routes.

b) Phosphate pH Uptake Profile

The procedure was as described in Example 7. The results are shown in Table 13 and 14 below.

TABLE 13

Guanidino resin (ex cyanamide)

| pH | Uptake* | uptake as % of pH4 uptake |
|---|---|---|
| 4.02 | 2.10 | |
| 4.80 | 2.23 | 106 |
| 5.63 | 2.24 | 107 |
| 6.48 | 1.98 | 94 |
| 7.24 | 1.88 | 90 |
| 8.00 | 1.91 | 91 |
| 8.70 | 1.74 | 83 |
| 9.36 | 1.70 | 81 |
| 10.25 | 1.50 | 72 |
| 10.99 | 1.08 | 52 |

TABLE 14

Guanidino resin (ex pyrazole reagent)

| pH | Uptake* | uptake as % of pH4 uptake |
|---|---|---|
| 4.01 | 2.11 | |
| 4.80 | 1.88 | 89 |
| 5.63 | 1.53 | 73 |
| 6.48 | 1.44 | 68 |
| 7.25 | 1.55 | 73 |
| 8.00 | 1.50 | 71 |
| 8.72 | 1.36 | 64 |
| 9.40 | 1.20 | 57 |
| 10.25 | 1.17 | 55 |
| 11.01 | 1.04 | 49 |

*mmol/g c) Competition Between Phosphate and Chloride. Complete Elution by Chloride of Phosphate The procedure and other details was as described in Example 8. The results are shown in Tables 15 and 16 below.

TABLE 15

Guanidinomethyl resin (ex cyanamide)

| | V | X | Y | Z |
|---|---|---|---|---|
| A | 5.42 | 163 | 73.9 | 4.01 |
| B | 1.51 | 75 | 61.3 | 11.2 |
| C | 3.57 | 179 | 32.6 | 13.2 |
| D | 1.10 | 55 | 24.4 | 25.6 |

TABLE 15-continued

Guanidinomethyl resin (ex cyanamide)

| | V | X | Y | Z |
|---|---|---|---|---|
| E | 0.644 | 32.2 | 19.2 | 34 |
| F | 0.439 | 22.0 | 15.7 | 40 |
| G | 1.22 | 61 | 5.89 | 22.2 |
| H | 0.373 | 18.6 | 2.91 | 29.5 |
| I | 0.144 | 7.2 | 1.75 | 41 |
| NaOH wash | | 10.9 | | |
| Total | | 623 | | |

TABLE 16

Guanidino resin (ex pyrazole reagent)

| | V | X | Y | Z |
|---|---|---|---|---|
| A | 4.91 | 147 | 76.0 | 4.48 |
| B | 1.51 | 76 | 63.6 | 11.5 |
| C | 3.25 | 163 | 37.0 | 15.5 |
| D | 1.145 | 57 | 27.7 | 28.3 |
| E | 0.709 | 35.5 | 21.9 | 38 |
| F | 0.501 | 25.1 | 17.8 | 40 |
| G | 1.17 | 58.5 | 8.22 | 27.8 |
| H | 0.521 | 26.1 | 3.96 | 29.3 |
| I | 0.260 | 13.0 | 1.84 | 28.1 |
| NaOH | | 11.3 | | |
| Total | | 612 | | |

EXAMPLE 10

Phosphate Uptake Experiments—Guanidinomethyl Group Containing Polymers Prepared from Highly Crosslinked Aminomethylpolystyrene a) Resins The highly crosslinked (degree of crosslinking unspecified) aminomethylpolystyrene was obtained from Purolite International Ltd and used to prepare guanidino resins via the cyanamide or pyrazole routes.

b) pH Phosphate Uptake Profile

This was carried out as described in Example 7. The results are shown in Tables 17 and 18 below.

TABLE 17

Guanidinomethyl resin (ex cyanamide)

| pH | Uptake* | uptake as % of pH4 uptake |
|---|---|---|
| 3.98 | 1.28 | |
| 4.99 | 1.04 | 81 |
| 5.77 | 0.98 | 77 |
| 6.41 | 0.86 | 67 |
| 7.22 | 0.76 | 59 |
| 8.00 | 0.68 | 53 |
| 8.68 | 0.59 | 46 |
| 9.36 | 0.55 | 43 |
| 10.09 | 0.48 | 38 |

TABLE 18

Guanidinomethyl resin (ex pyrazole reagent)

| pH | Uptake* | uptake as % of pH4 uptake |
|---|---|---|
| 4.00 | 1.70 | |
| 4.78 | 1.28 | 75 |
| 5.67 | 1.11 | 65 |
| 6.42 | 0.99 | 58 |
| 7.24 | 0.82 | 48 |
| 8.00 | 0.70 | 41 |
| 8.65 | 0.59 | 35 |
| 9.36 | 0.55 | 33 |
| 10.24 | 0.47 | 28 |
| 11.01 | 0.39 | 23 |

*mmol/g

The profiles are very similar to those of comparable resins prepared from 2% crosslinked polystyrene. However the absolute phosphate uptake was appreciably lower than that obtained with 2% crosslinked resins. The findings are compatible with the expectation that the functional groups in this resin are the same as the 2% crosslinked.

c) Competition Between Phosphate and Chloride. Complete Elution by Chloride of Phosphate The procedure was as described in Example 8. The results are shown in Tables 19 and 20 below.

TABLE 19

Guanidino resin (ex cyanamide)

| | V | X | Y | Z |
|---|---|---|---|---|
| A | 8.71 | 262 | 48.2 | 2.13 |
| B | 2.30 | 69 | 34.8 | 4.5 |
| C | 2.63 | 132 | 7.55 | 8.9 |
| D | 0.380 | 19.0 | 3.8 | 15.0 |
| E | 0.171 | 8.6 | 2.3 | 18.8 |
| F | 0.121 | 6.1 | 1.1 | 35 |
| NaOH wash | | 5.6 | | |
| Total | | 502 | | |

TABLE 20

Guanidinomethyl resin (ex pyrazole reagent)

| | V | X | Y | Z |
|---|---|---|---|---|
| A | 8.08 | 242 | 48.7 | 2.30 |
| B | 1.68 | 51 | 37.8 | 6.45 |
| C | 2.455 | 123 | 11.9 | 9.7 |
| D | 0.545 | 27.3 | 6.05 | 16.4 |
| E | 0.248 | 12.4 | 3.4 | 19.2 |
| F | 0.245 | 12.2 | 0.8 | 22.0 |
| NaOH wash | | 3.9 | | |
| Total | | 472 | | |

The purpose of this experiment is to show the unsuitability of highly crosslinked polymers in the present invention because of its poor phosphate-uptake characteristics. All the highly crosslinked resins had low affinity for phosphate relative to chloride. The high degree of crosslinkinc, probably hinders entry of the phosphate into the resin.

EXAMPLE 11

Anion Competition Experiments

The purpose of these studies is to show that, with the exception of sulphate, the guanidinomethylpolystyrene, 2% crosslinked retains phosphate effectively in the presence of other anions. This is indicative therefore of the likely clinical efficacy of the polymers of the invention.

The resin used in this study was prepared from guanidinomethylpolystyrene, 2% crosslinked which was obtained as a fine powder from Purolite International Ltd.

Since some of the anions are difficult or impossible to use at pH 7 because of insolubility of the free acid or instability of the anions, it was decided to proceed at pH 8 instead. Thus 20 g batches of the resins were suspended in water containing 10 ml of phosphoric acid and equilibrated at pH 8.00 using NaOH. They were filtered, washed thoroughly with water and dried overnight at about 70°. Since bicarbonate was difficult to handle at this pH, resin was prepared for these experiments at pH 8.6 (see below).

The results are shown below.

TABLE 21

Equilibrium between phosphate-loaded guanidinomethyl resins and 25 mM NaCl

| Sample | Wt. of resin (mg) | Vol. (ml) | Pi in supernatant Conc. (mM) | Pi in supernatant Total (µmol) | Pi retained Total (µmol) | Pi retained % | Total Pi (µmol) | Z |
|---|---|---|---|---|---|---|---|---|
| 1 | 705 | 40 | 3.78 | 152 | 780 | 83.8 | 935 | 5.55 |
| 2 | 705 | 200 | 1.32 | 2.64 | 685 | 72.2 | 950 | 13.05 |
| 3 | 350 | 400 | 0.505 | 202 | 265 | 56.8 | 465 | 28.3 |
| 4 | 350 | 700 | 0.39 | 235 | 233 | 49.8 | 470 | 31.9 |
| 5 | 350 | 1000 | 0.28 | 278 | 203 | 42.2 | 480 | 38.0 |

TABLE 22

Equilibrium between phosphate-loaded guanidinomethyl resins and 100 mM NaCl

| Sample | Wt. of resin (mg) | Vol. (ml) | Pi in supernatant Conc. (mM) | Pi in supernatant Total (µmol) | Pi retained Total (µmol) | Pi retained % | Total Pi (µmol) | Z |
|---|---|---|---|---|---|---|---|---|
| 1 | 175 | 400 | 0.421 | 187 | 51 | 21.5 | 238 | 51.2 |
| 2 | 177 | 700 | 0.263 | 205 | 37.5 | 15.4 | 243 | 58.5 |
| 3 | 176 | 1000 | 0.190 | 212 | 30.1 | 12.4 | 242 | 65.5 |
| 4 | 176 | 1500 | 0.132 | 224 | 22.2 | 9.9 | 248 | 75 |
| 5 | 101 | 2000 | 0.165 | 137 | 6.15 | 4.3 | 143 | 70 |

TABLE 23

Equilibrium between phosphate-loaded guanidinomethyl resins and 5 mM $Na_2SO_4$

| Sample | Wt. of resin (mg) | Vol. (ml) | Pi in supernatant Conc. (mM) | Pi in supernatant Total (µmol) | Pi retained Total (µmol) | Pi retained % | Total Pi (µmol) | Z |
|---|---|---|---|---|---|---|---|---|
| 1 | 709 | 200 | 2.88 | 575 | 333 | 37 | 908 | 0.66 |
| 2 | 708 | 400 | 1.89 | 755 | 182 | 20 | 937 | 0.52 |
| 3 | 351 | 400 | 1.11 | 423 | 40 | 9 | 463 | 0.38 |
| 4 | 353 | 1000 | 0.49 | 491 | 11 | 2.2 | 502 | 0.22 |

TABLE 24

Equilibrium between phosphate-loaded guanidinomethyl resins and 25 mM sodium acetate

| Sample | Wt. of resin (mg) | Vol. (ml) | Pi in supernatant Conc. (mM) | Pi in supernatant Total ($\mu$mol) | Pi retained Total ($\mu$mol) | Pi retained % | Total Pi ($\mu$mol) | Z |
|---|---|---|---|---|---|---|---|---|
| 1 | 708 | 200 | 0.88 | 176 | 658 | 79 | 834 | 22.5 |
| 2 | 709 | 400 | 0.555 | 224 | 598 | 73 | 822 | 32.7 |
| 3 | 356 | 400 | 0.345 | 138 | 266 | 66 | 404 | 47.8 |
| 4 | 358 | 700 | 0.24 | 169 | 247 | 59.5 | 416 | 61.5 |
| 5 | 356 | 1000 | 0.185 | 187 | 239 | 56 | 426 | 79 |

TABLE 25

Equilibrium between phosphate-loaded guanidinomethyl resins and 100 mM sodium acetate

| Sample | Wt. of resin (mg) | Vol. (ml) | Pi in supernatant Conc. (mM) | Pi in supernatant Total ($\mu$mol) | Pi retained Total ($\mu$mol) | Pi retained % | Total Pi ($\mu$mol) | Z |
|---|---|---|---|---|---|---|---|---|
| 1 | 177 | 400 | 0.399 | 160 | 64 | 28.7 | 224 | 72 |
| 2 | 177 | 700 | 0.256 | 179 | 49.7 | 21.7 | 229 | 85 |
| 3 | 175 | 1000 | 0.190 | 190 | 40.5 | 17.6 | 231 | 93 |

TABLE 26

Equilibrium between phosphate-loaded guanidinomethyl resins and 250 mM sodium acetate

| Sample | Wt. of resin (mg) | Vol. (ml) | Pi in supernatant Conc. (mM) | Pi in supernatant Total ($\mu$mol) | Pi retained Total ($\mu$mol) | Pi retained % | Total Pi ($\mu$mol) | Z |
|---|---|---|---|---|---|---|---|---|
| 1 | 179 | 600 | 0.378 | 227 | 18.5 | 7.5 | 246 | 50 |
| 2 | 176 | 1000 | 0.234 | 234 | 12.8 | 5.2 | 247 | 55 |
| 3 | 108 | 1000 | 0.154 | 154 | 5.7 | 3.55 | 160 | 58 |

TABLE 27

Equilibrium between phosphate-loaded guanidinomethyl resins and 10 mM sodium bicarbonate

| Sample | Wt. of resin (mg) | Vol. (ml) | Pi in supernatant Conc. (mM) | Pi in supernatant Total ($\mu$mol) | Pi retained Total ($\mu$mol) | Pi retained % | Total Pi ($\mu$mol) | Z |
|---|---|---|---|---|---|---|---|---|
| 1 | 503 | 100 | 1.105 | 111 | 447 | 80 | 558 | 7.25 |
| 2 | 623 | 250 | 0.795 | 198 | 457 | 70 | 655 | 8.85 |
| 3 | 622 | 500 | 0.525 | 262 | 422 | 61.5 | 684 | 11.8 |
| 4 | 426 | 500 | 0.425 | 213 | 278 | 56.5 | 491 | 13.3 |
| 5 | 498 | 1000 | 0.297 | 297 | 285 | 49 | 582 | 16.5 |

TABLE 28

Equilibrium between phosphate-loaded guanidinomethyl resins and 25 mM sodium bicarbonate

| Sample | Wt. of resin (mg) | Vol. (ml) | Pi in supernatant Conc. (mM) | Pi in supernatant Total ($\mu$mol) | Pi retained Total ($\mu$mol) | Pi retained % | Total Pi ($\mu$mol) | Z |
|---|---|---|---|---|---|---|---|---|
| 1 | 314 | 500 | 0.512 | 256 | 110 | 30 | 366 | 14.6 |
| 2 | 366 | 1000 | 0.337 | 337 | 107 | 24 | 444 | 17.9 |
| 3 | 257 | 1000 | 0.257 | 257 | 65 | 20 | 322 | 19.7 |
| 4 | 163 | 1000 | 0.180 | 180 | 26.5 | 12.8 | 207 | 17.8 |
| 5 | 77 | 1000 | 0.092 | 92 | 7.25 | 7.3 | 99 | 20.0 |

TABLE 29

Equilibrium between phosphate-loaded guanidinomethyl resins and 10 mM sodium cholate

| Sample | Wt. of resin (mg) | Vol. (ml) | Pi in supernatant Conc. (mM) | Pi in supernatant Total ($\mu$mol) | Pi retained Total ($\mu$mol) | Pi retained % | Total Pi ($\mu$mol) | Z |
|---|---|---|---|---|---|---|---|---|
| 1 | 354 | 100 | 1.41 | 141 | 235 | 62.5 | 376 | 4.45 |
| 2 | 359 | 200 | 0.775 | 155 | 233 | 58.5 | 398 | 7.6 |
| 3 | 184 | 200 | 0.405 | 81 | 127 | 61 | 208 | 15.1 |
| 4 | 183 | 350 | 0.205 | 72 | 133 | 63.5 | 209 | 29.5 |
| 5 | 181 | 500 | 0.155 | 77 | 115 | 60 | 192 | 38 |

TABLE 30

Equilibrium between phosphate-loaded guanidinomethyl resins and 25 mM sodium cholate

| Sample | Wt. of resin (mg) | Vol. (ml) | Pi in supernatant Conc. (mM) | Pi in supernatant Total ($\mu$mol) | Pi retained Total ($\mu$mol) | Pi retained % | Total Pi ($\mu$mol) | Z |
|---|---|---|---|---|---|---|---|---|
| 1 | 184 | 350 | 0.214 | 75 | 127 | 62.5 | 202 | 73 |
| 2 | 182 | 700 | 0.130 | 91 | 124 | 57.5 | 215 | 111 |

TABLE 31

Equilibrium between phosphate-loaded guanidinomethyl resins and 10 mM sodium taurocholate

| Sample | Wt. of resin (mg) | Vol. (ml) | Pi in supernatant Conc. (mM) | Pi in supernatant Total ($\mu$mol) | Pi retained Total ($\mu$mol) | Pi retained % | Total Pi ($\mu$mol) | Z |
|---|---|---|---|---|---|---|---|---|
| 1 | 358 | 100 | 0.895 | 90 | 305 | 77 | 395 | 8.6 |
| 2 | 360 | 200 | 0.60 | 120 | 309 | 72 | 429 | 12.0 |
| 3 | 180 | 200 | 0.33 | 66 | 145 | 69 | 211 | 20.9 |
| 4 | 117 | 300 | 0.162 | 49 | 97 | 66 | 146 | 42 |
| 5 | 118 | 700 | 0.101 | 71 | 94 | 57 | 165 | 56 |

The results show that with acetate and bicarbonate, acetate is not as good as chloride and bicarbonate is better than chloride for displacing phosphate.

Sulphate, in agreement with previous results, displaces phosphate efficiently; indeed it binds more firmly to the resin than phosphate. However, sulphate is not a physiologically important anion and thus not relevant to the present invention.

Cholate readily displaced 40% of the total phosphate from the resin; however, it was totally ineffective at displacing further phosphate from the resin.

We claim:

1. A method of treatment of a patient which comprises administering to said patient a polystyrene polymer cross-linked by 1.5% to 8% with divinylbenzene based on the total weight of the polymer and having a minimum weight average molecular weight of 10,000 wherein 50–100% of the aromatic groups of the polystyrene are substituted by at least one $(R^1)_n$—$NHR^2$ group wherein $R^1$ represents a straight or branched chain alkylene or cycloalkylene group of 1 to 6 carbon atoms and n is 0 or 1 and $NHR^2$ represents a guanidino group of formula —NH—C(=NH)NH$_2$ or a biguanidino group of formula —NH—C(=NH)—NH—C(=NH)—NH$_2$, in order to control phosphate uptake from the diet and/or remove excess phosphate from the bloodstream.

* * * * *